(12) United States Patent
Trevino

(10) Patent No.: US 7,798,422 B2
(45) Date of Patent: Sep. 21, 2010

(54) CEDAR OIL EVAPORATORS

(76) Inventor: Ruben E. Trevino, 975 Birchwood Dr., Clover, SC (US) 29710

( * ) Notice: Subject to any disclaimer, the term of this patent is extended or adjusted under 35 U.S.C. 154(b) by 0 days.

(21) Appl. No.: 12/176,410

(22) Filed: Jul. 21, 2008

(65) Prior Publication Data

US 2009/0020625 A1 Jan. 22, 2009

Related U.S. Application Data

(60) Provisional application No. 60/950,769, filed on Jul. 19, 2007.

(51) Int. Cl.
*A61L 9/04* (2006.01)
(52) U.S. Cl. .......................... 239/44; 239/51.5; 239/57; 239/145; 239/326
(58) Field of Classification Search ............. 239/34–60, 239/145, 326; 43/1
See application file for complete search history.

(56) References Cited

U.S. PATENT DOCUMENTS

| 929,254 | A | * | 7/1909 | Sholes | ......................... 239/45 |
| 1,863,511 | A | | 6/1932 | Travis | |
| 2,111,025 | A | | 3/1938 | Galler | |
| 2,383,960 | A | * | 9/1945 | Dupuy | ...................... 239/51.5 |
| 4,352,457 | A | | 10/1982 | Weick | |
| 4,413,779 | A | * | 11/1983 | Santini | ......................... 239/45 |
| 4,621,768 | A | | 11/1986 | Lhoste | |
| 5,038,394 | A | * | 8/1991 | Hasegawa et al. | ............ 392/395 |
| 5,246,919 | A | * | 9/1993 | King | ............................. 512/4 |
| 6,820,363 | B1 | | 11/2004 | Averette | |
| 6,921,025 | B2 | | 7/2005 | Hart | |
| 7,055,764 | B1 | * | 6/2006 | Martinez et al. | ............. 239/145 |
| 2007/0290064 | A1 | * | 12/2007 | Majerowski et al. | ........... 239/44 |

FOREIGN PATENT DOCUMENTS

GB 2047537 A * 12/1980

* cited by examiner

*Primary Examiner*—Len Tran
*Assistant Examiner*—Jason J Boeckmann
(74) *Attorney, Agent, or Firm*—Tillman Wright, PLLC; Chad D. Tillman; James D. Wright

(57) ABSTRACT

A cedar oil evaporator includes: a housing having openings therein for ventilation of air; a reservoir within the housing containing cedar oil; and a carrier for wicking away the cedar oil from the reservoir for dispersing cedar oil via air that passes through the housing. Each carrier is a length of cotton twine having a diameter of one-sixteenth of an inch or smaller and a length of twelve and one-half feet or longer. The housing includes a door movable about a hinge between a first position, wherein the reservoir is accessible for removal from the housing; and a second position, wherein the reservoir is inaccessible for removal. An extent of the carrier that is received within the reservoir for immersion in the cedar oil preferably represents 10% or less of the overall length of the carrier, the remainder being randomly exposed within the interior space of the housing.

12 Claims, 16 Drawing Sheets

CEDAR OIL EVAPORATORS

CROSS-REFERENCE TO RELATED APPLICATION

The present application is a U.S. nonprovisional patent application of, and claims priority under 35 U.S.C. §119(e) to, U.S. provisional patent application Ser. No. 60/950,769, filed Jul. 19, 2007, which provisional patent application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to apparatus for evaporating a liquid and, more particularly, to apparatus for evaporating cedar oil.

It is known that cedar oil works well in warding off moths and other undesirable creatures. Indeed cedar closets—closets lined with cedar wood having natural cedar oil therein—have been a popular amenity when constructing or refurbishing homes because of the ability of the cedar closets to naturally ward off moths from clothes and coats that may be stored in the closets. A drawback to cedar closets are the expenses associated with their construction. An additional drawback is that cedar closets lose their effectiveness over time as the natural cedar oil evaporates from the cedar wood lining. As a result, cedar closets can be renewed by sanding of the cedar wood lining. The cedar wood can also be renewed by application of cedar oil to the wood lining, some of which is slowly absorbed by the cedar wood. As will be apparent, however, the renewal of a cedar closet can be both time and labor intensive. Moreover, the renewal of a cedar closet requires that the items otherwise stored in the closet be relocated during the renewal period. As may be expected, many homeowners choose not to renew their cedar closets and thereby avoid such time, expense and hassle; however, in doing so, they lose the benefit of protection of their coats and clothes provided by the cedar closets against moths and other creatures that they previously enjoyed.

Alternatives to cedar closets include the use of moth balls or other chemicals that may be placed in closets and that also ward off moths. Unfortunately, such other measures often have an unpleasant smell associated with them. Indeed, clothes and coats stored in a closet that includes moth balls often must be dry cleaned before such clothes and coats are suitable for wearing because they acquire the "moth ball" smell.

Another alternative to cedar closets is disclosed in Travis U.S. Pat. No. 1,863,511, which is incorporated herein by reference. Travis discloses the use of a box containing cedar shavings. The shavings are retained within the box and openings are provided in the walls of the box for ventilation and release of evaporated cedar oil. The box may be placed in a dresser drawer or suspended in a closet by a coat hanger and serves to provide a cedar smell that is given off by the natural cedar oil contained in the cedar shavings. While believed suitable for its stated intended purpose, it is believed that the effectiveness of the device of Travis diminishes quickly over time as the cedar oil evaporates from the cedar shavings. Indeed, recognizing the limited life of the box, Travis discloses that the box should be kept sealed until ready for actual use, else it may become useless.

Still yet another alternative to cedar closets is disclosed in Galler U.S. Pat. No. 2,111,025, which is incorporated herein by reference. Galler discloses the combined use of paradichlorbenzene (which is used in moth balls) for warding off of moths, in conjunction with cedar oil for masking the smell of the paradichlorbenzene. Galler expressly teaches that "cedar oil is not as effective for moth prevention purposes as might be desired" but that cedar "possesses the valuable property of having a powerful, aromatic odor, considered pleasant by most people." Like the device in Travis, the device in Galler may be hung in a closet using a hook similar to that of a clothes hanger. While believed suitable for its stated intended purpose, it is believed that clothes and coats protected by the device of Galler nevertheless will smell of moth balls and will therefore need to be dry cleaned prior to use.

In addition to the foregoing known devices, evaporators for liquid perfumes and deodorizers are known and disclosed, for example, in U.S. Pat. Nos. 6,921,025; 4,621,768; and 4,352,457, each of which is incorporated herein by reference. However, none of these devices are intended to be used for the evaporation of cedar oil to provide an equivalent means to obtaining the benefits of a new or revitalized cedar closet.

Accordingly, it is believed that a need exists for a device that provides the benefits of a new or revitalized cedar closet and that is simple to manufacture and use. It furthermore is believed that need exists for such a device that is "green", i.e., that is reusable and not a disposable, single-use device. It is believed that one or more of these needs are addressed by one or more embodiments of the invention.

SUMMARY OF THE INVENTION

The present invention includes many aspects and features.

Accordingly, in one aspect of the invention, A cedar oil evaporator includes: a housing having openings therein for the ventilation of air; a single reservoir for containing cedar oil, the single reservoir being contained within the housing; and a plurality of carriers each for wicking away the cedar oil from the single reservoir for dispersing cedar oil via air that passes through the housing.

In a feature of this aspect, there are four carriers.

In a feature of this aspect, each carrier is formed from a length of cotton twine.

In a feature of this aspect, each carrier is made from a length of material having a diameter that is approximately one-sixteenth of an inch or smaller.

In a feature of this aspect, each carrier is formed from a length of material that is approximately twelve and one-half feet or longer.

In a feature of this aspect, each carrier is made from a length of cotton twine that is approximately twelve and one-half feet or longer and that has a diameter that is approximately one-sixteenth of an inch or smaller.

In a feature of this aspect, the single reservoir includes a basin and a cover, wherein the basin and cover define an interior space for holding of the cedar oil. Furthermore, the cover includes a plurality of openings for receipt therethrough of the plurality of carriers.

In a feature of this aspect, the single reservoir is removable from the housing.

In a feature of this aspect, the housing includes a door that is movable about a hinge between a first position, wherein an interior space of the housing is accessible for removal of the reservoir from the housing; and a second position, wherein the space of the container is inaccessible for removable of the reservoir from the housing.

In a feature of this aspect, the single reservoir includes cedar oil and each of the carriers is partially immersed in the cedar oil within the single reservoir. Furthermore, an extent of each carrier that is received within the single reservoir for immersion in the cedar oil preferably represents 10% or less of the overall length of the carrier, the remainder of the carrier being contained within the interior space of the housing whereby a large surface area of the carrier is exposed to air that passes through the ventilation openings in the housing.

In another feature, the extent of each carrier that is exposed to the air passing through the housing is randomly disposed within the interior housing of the container.

In another aspect of the invention, a cedar oil evaporator includes: a housing having openings therein for the ventilation of air; a plurality of reservoirs each for containing cedar oil, each of the plurality of reservoirs being contained within the housing; and a plurality of carriers each for wicking away the cedar oil from the single reservoir for dispersing cedar oil via air that passes through the housing.

In a feature of this aspect, each reservoir includes a self-enclosed container of cedar oil.

In a feature of this aspect, the plurality of reservoirs consists of four reservoirs and wherein the plurality of carriers includes four carriers, each one of the four carriers extending from a respective one of the reservoirs.

In another feature, the extent of each carrier that is exposed to the air passing through the housing is randomly disposed within the interior housing of the container.

In additional features of this aspect, each reservoir of the plurality of reservoirs includes a bottle of cedar oil; a respective carrier of the plurality of carriers extends from within a respective one of the bottles of cedar oil; the housing includes a door that is movable about a hinge between a first position, wherein an interior space of the housing is accessible for removal of the bottles from the housing, and a second position, wherein the interior space of the container is inaccessible for removable of the bottles from the housing; and an extent of each carrier that is received within a respective bottle for immersion in the cedar oil represents 10% or less of the overall length of the carrier, the remainder of the carrier being contained within the interior space of the housing whereby a large surface area of the carrier is exposed to air that passes through the ventilation openings in the housing.

In another feature of this aspect, the housing includes a rectangular container.

In another aspect, a cedar oil evaporator includes: a circular container having openings therein for the ventilation of air; and a carrier having a length that is randomly received and contained within with circular container, the carrier being saturated with cedar oil, whereby the cedar oil evaporates into air that passes through the openings in the circular container.

In a feature of this aspect, the carrier is made from a length of cotton twine that is approximately twelve and one-half feet or longer and that has a diameter that is approximately one-sixteenth of an inch or smaller.

In a feature of this aspect, the carrier is randomly contained within the circular container.

In a feature of this aspect, the circular container is shaped like a puck. Furthermore, the circular container preferably includes upper and lower circular portions that are releasable attached to one another about the circumference of the circular container, and wherein only the upper circular portion includes the openings for the ventilation of air.

In addition to the aforementioned aspects and features of the present invention, it should be noted that the present invention further encompasses the various possible combinations of such aspects and features.

BRIEF DESCRIPTION OF THE DRAWINGS

One or more preferred embodiments of the invention is disclosed in the accompanying drawings, wherein like elements are referred to with like reference numerals, and wherein.

DETAILED DESCRIPTION

Figure 1:
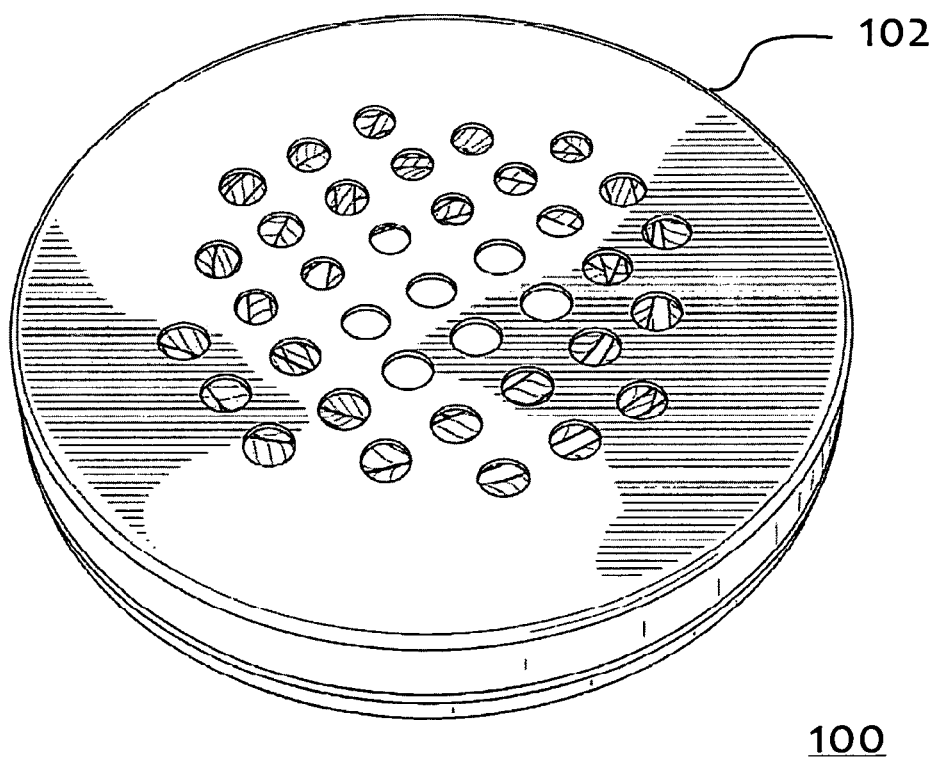
FIG. 1 is a perspective view of a cedar oil evaporator for use in a drawer in accordance with an embodiment of the invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Figure 2:
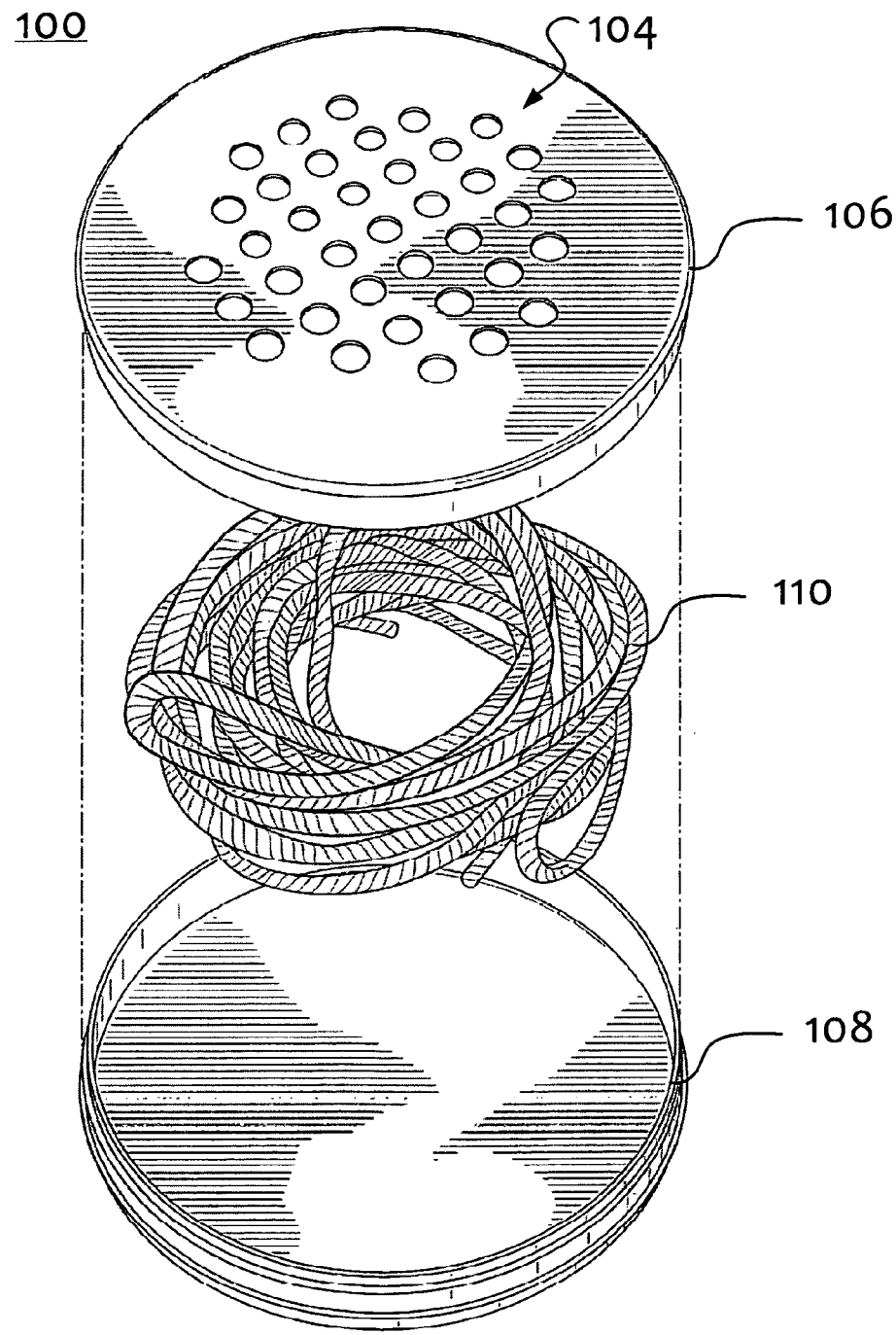
FIG. 2 is an exploded view of the evaporator of FIG. 1.

Turning to FIGS. 1-2, a cedar oil evaporator 100 in accordance with a first embodiment of the invention is illustrated. Specifically, FIG. 1 is a perspective view of the cedar oil evaporator 100, and FIG. 2 is an exploded view of the evaporator 100. The evaporator preferably is intended for use in a dresser drawer.

The evaporator 100 includes a circular container 102 having openings 104 formed in a top 106 thereof for the ventilation of air. The evaporator 100 also includes a large length of cotton twine 110 that has been saturated in cedar oil such that the cotton twine 110 disperses the cedar oil via the ventilated air. The cotton twine 110 is randomly disposed within the circular container 102. In contrast to the other illustrated embodiments herein, no openings are formed in the bottom 108 of the container 102, and the evaporator 100 does not include any reservoir of cedar oil.

Figure 3:
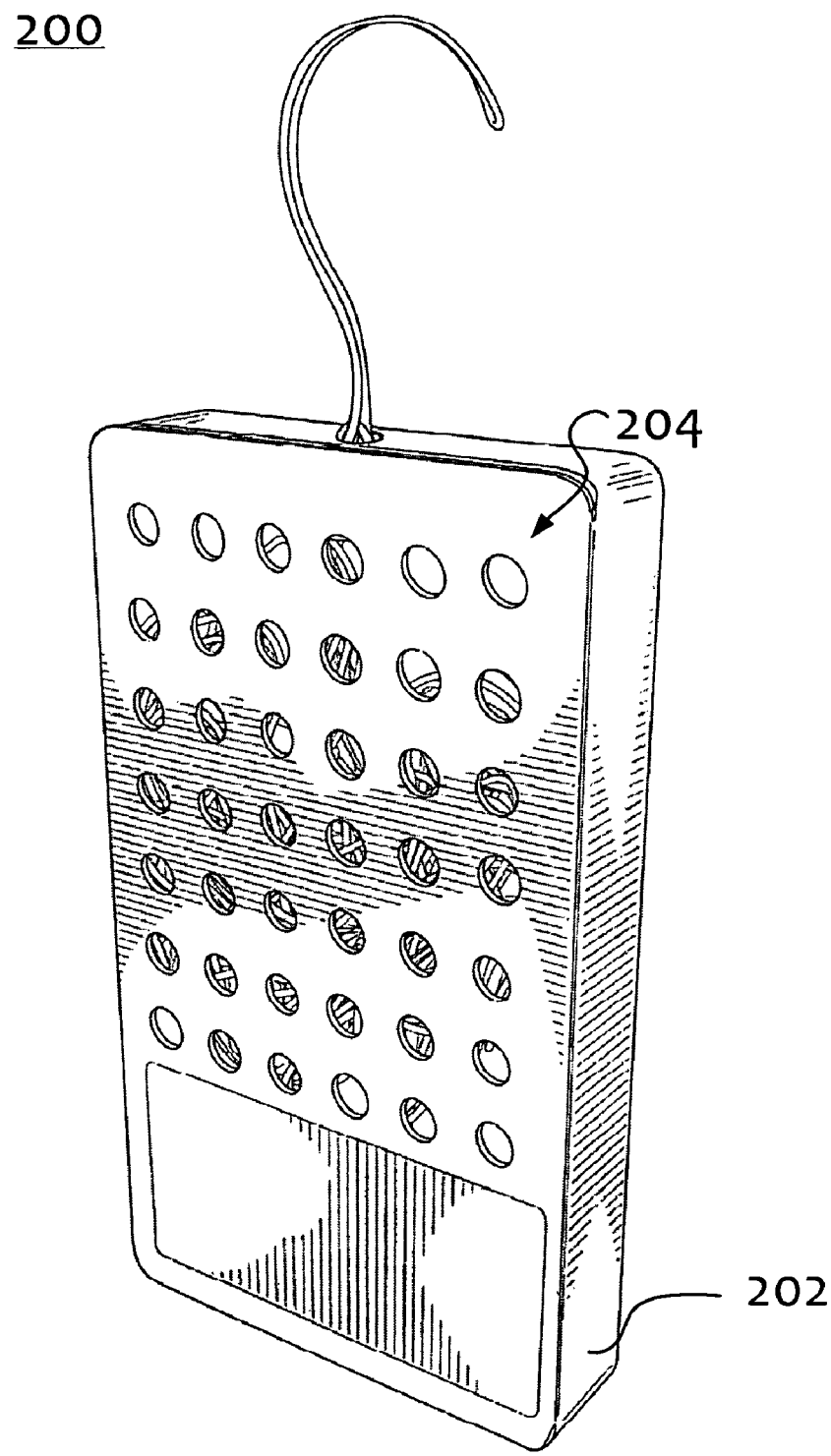
FIG. 3 is a perspective view of a cedar oil evaporator for use in a closet in accordance with another embodiment of the invention.
Figure 4:
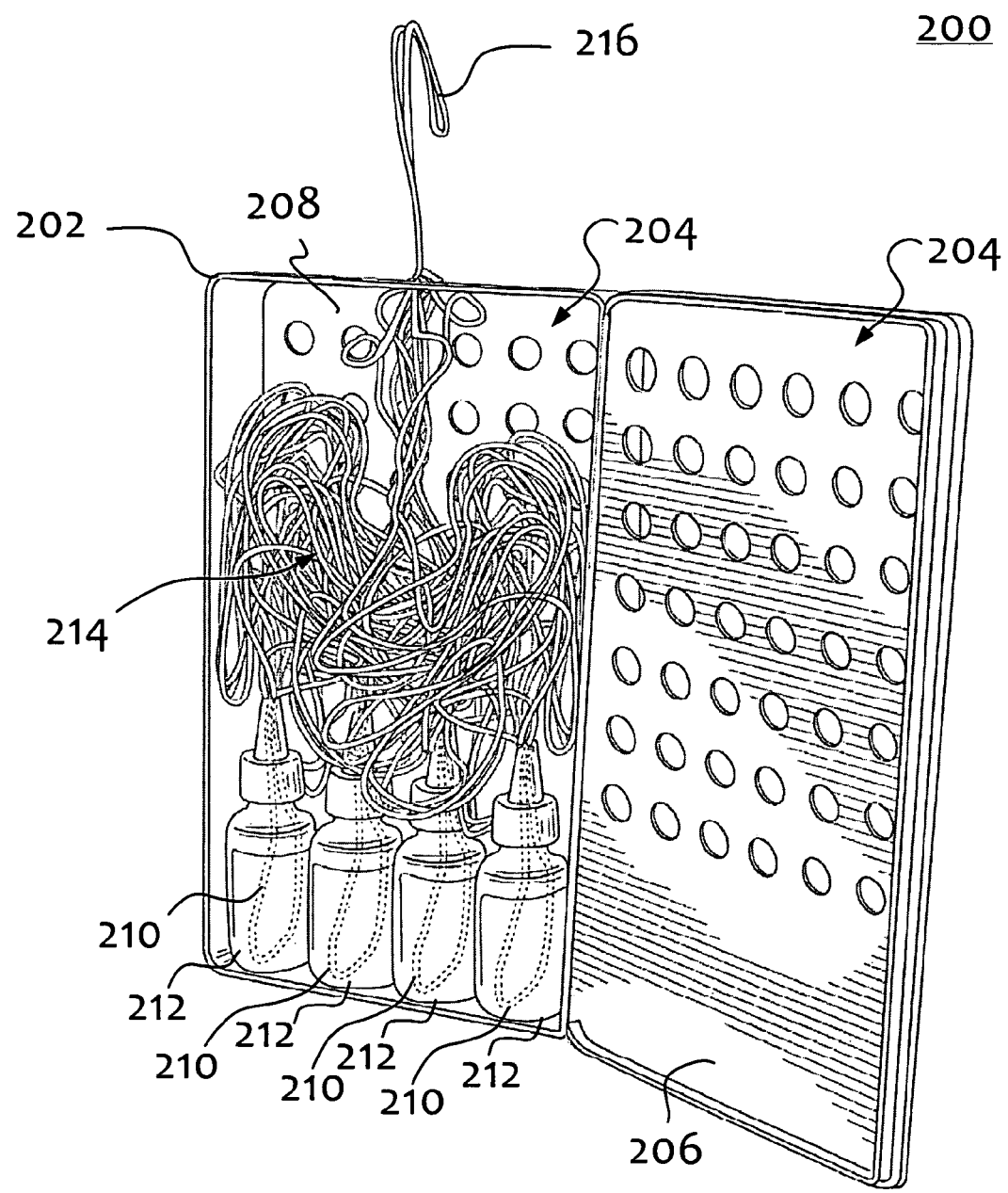
FIG. 4 is a perspective view similar to that of FIG. 3 with the door thereof open for showing the interior thereof.

Turning now to FIGS. 3-4, a cedar oil evaporator 200 in accordance with a second embodiment of the invention is illustrated. Specifically, FIG. 3 is a perspective view of the cedar oil evaporator 200, and FIG. 4 is a perspective view similar to that of FIG. 3, wherein a door 206 of a housing 202 of the evaporator is open for showing the interior thereof. The cedar oil evaporator 200 preferably is intended for use in a closet for the protection of coats and clothes from moths.

The cedar oil evaporator 200 includes openings 204 formed in the door 206 and in a back wall 208 of the rectangular housing 202, which openings 204 are for the ventilation of air therethrough. The evaporator 200 further includes four separate lengths 210 of cotton twine. Each length 210 of cotton twine extends from a bottle 212 of cedar oil (or reservoir of cedar oil) and includes a portion thereof that is immersed in the cedar oil within the bottle for wicking of the cedar oil out of the bottle. Furthermore, each length 210 of cotton twine preferably has a great length with the portion of the cotton twine that is immersed in the bottle being a very small extent of the overall length 210 of the cotton twine. Indeed, this immersed portion preferably represents 10% or less of the overall length 210 of the cotton twine. The remainder of each of cotton twine length 210 is randomly contained within the interior space of the evaporator 200 (i.e., bunched as shown 214 in FIG. 4) in such a manner that a large surface area of each of the cotton twine lengths 210 is exposed to air that passes through the ventilation openings 204 in the housing 202. It will be appreciated from FIG. 4 that the cotton twine lengths 210 define a plurality of interstices through which air can pass. It is believed that the cedar oil is wicked from each bottle 212 through each extent of the cotton twine lengths 210 and is dispersed via the ventilated air. A wire forms a hook 216 and extends from the top of the housing 202 of the evaporator 200 for the preferred hanging of the evaporator 200 in a closet.

Figure 5:
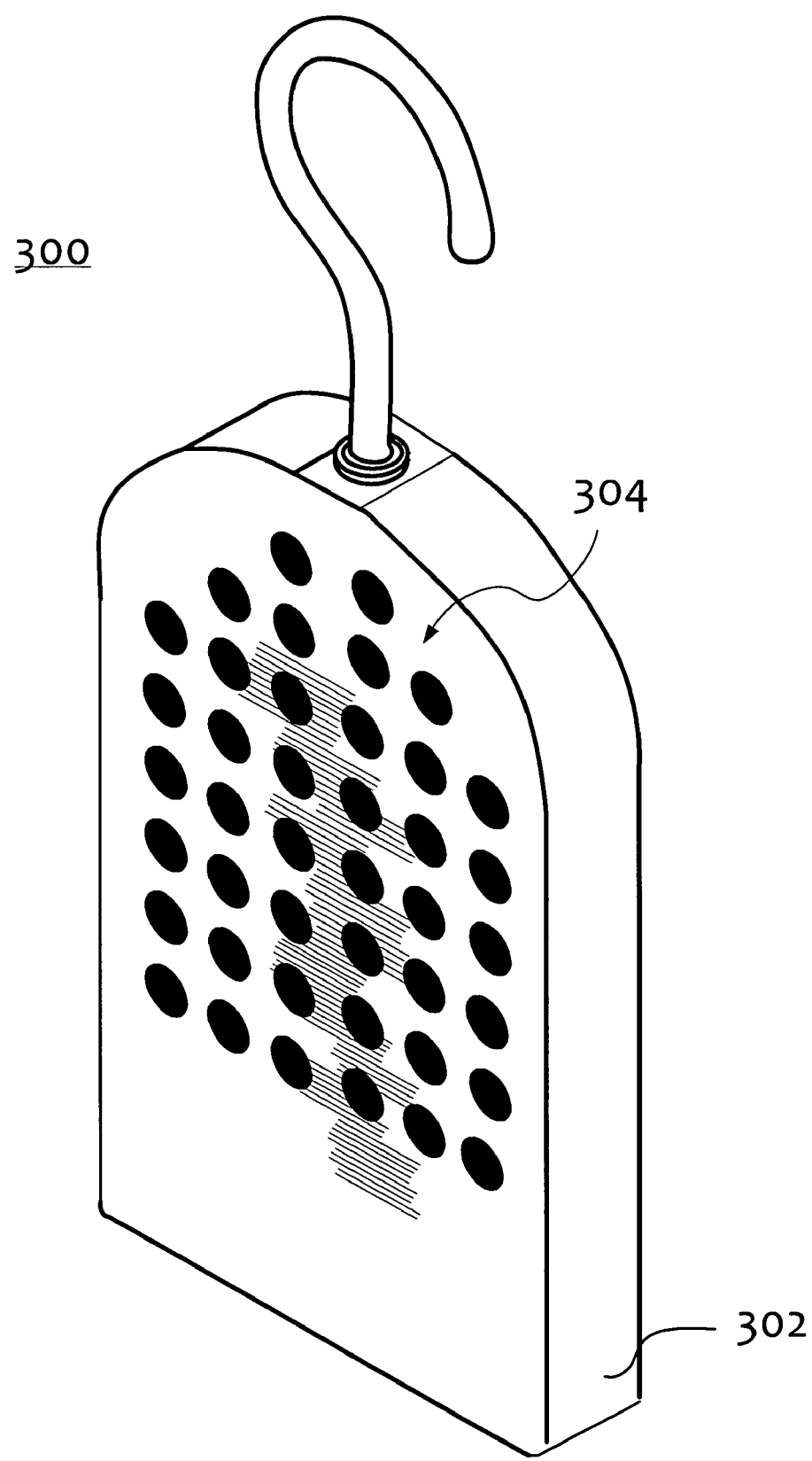
FIG. 5 is a perspective view of a third cedar oil evaporator for use in a closet in accordance with a third embodiment of the invention.
Figure 6:
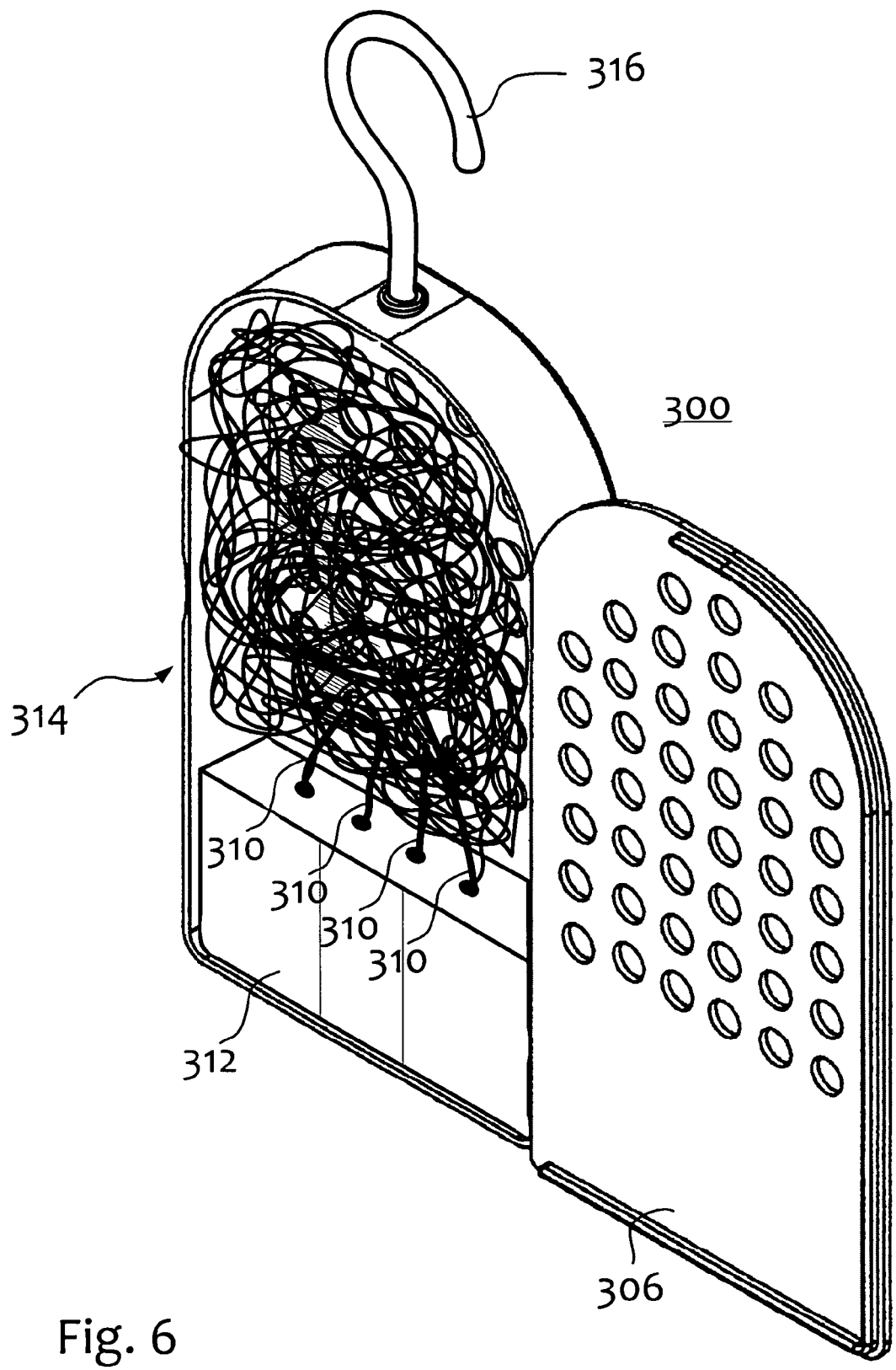
FIG. 6 is a perspective view of the third cedar oil evaporator of FIG. 5 with the door thereof open for showing the interior thereof.

FIGS. 5-9 illustrate another cedar oil evaporator 300 in accordance with a third embodiment of the invention. Specifically, FIG. 5 is a perspective view of the cedar oil evaporator 300; FIG. 6 is a perspective view similar to that of FIG.

Figure 7:
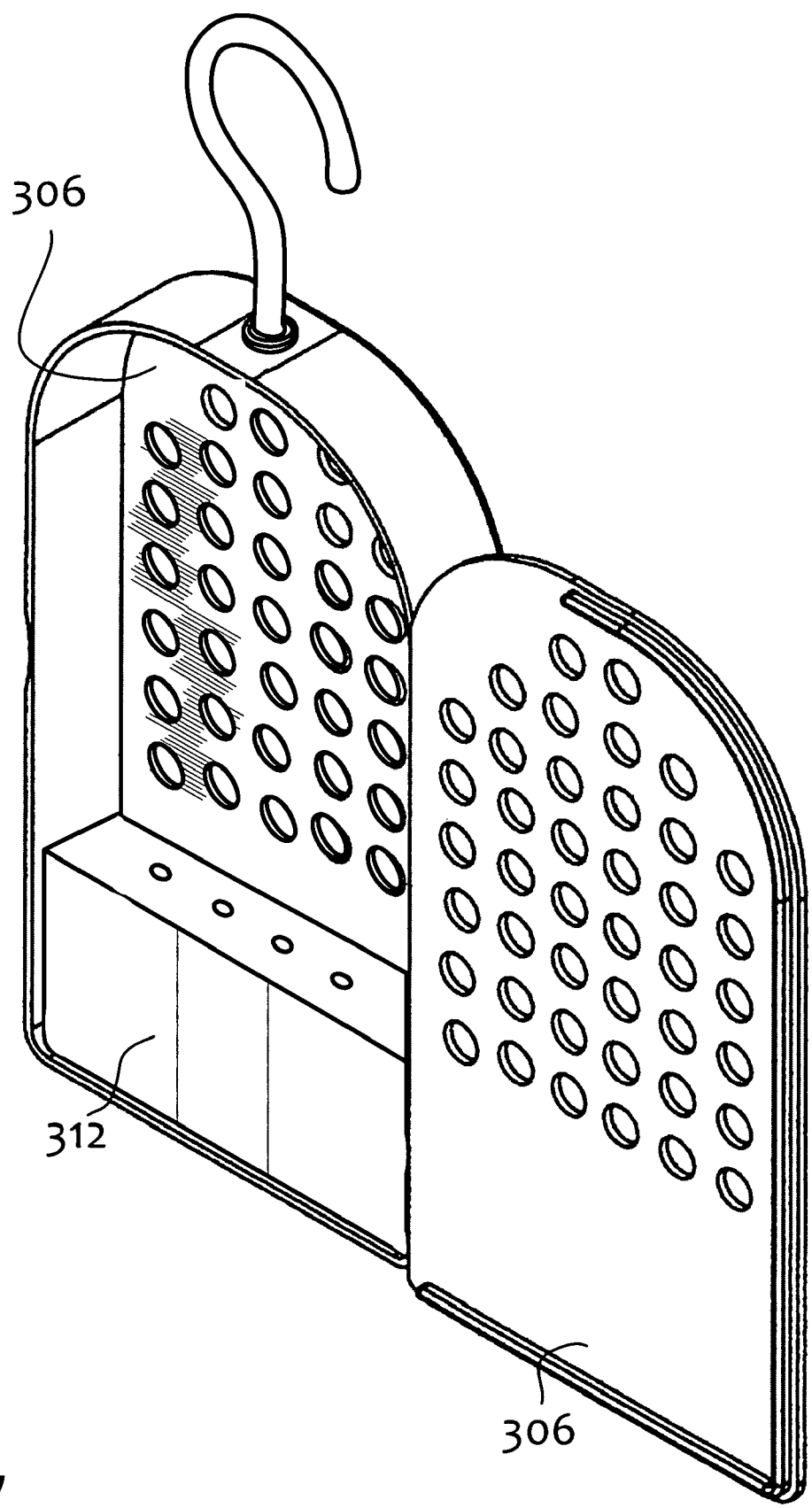
FIG. 7 is a perspective view similar to that of FIG. 6, wherein the cotton-twine wicks have been omitted for clarity of illustration.
Figure 7A:
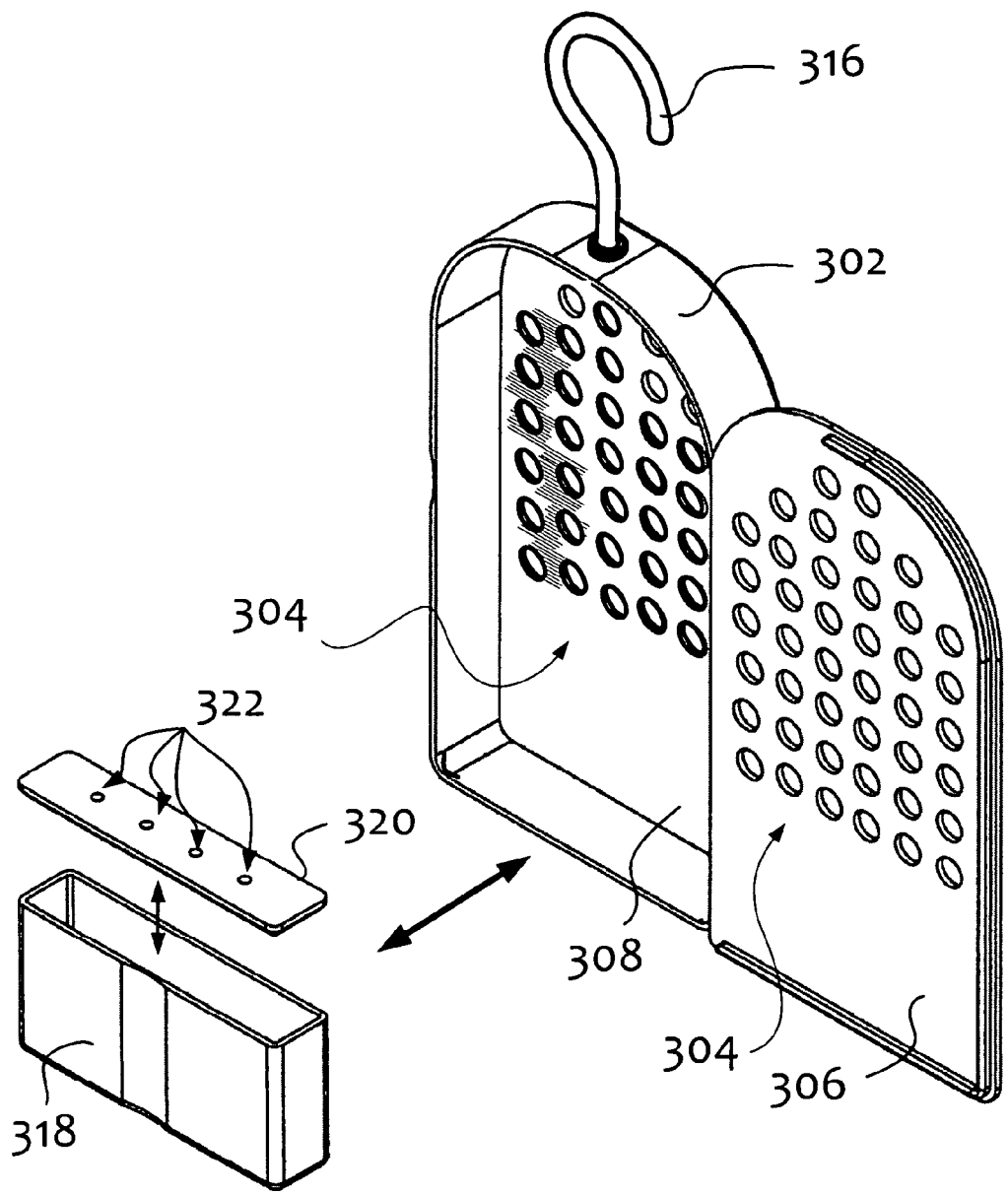
FIG. 7A is a perspective exploded view of certain of the components of the cedar oil evaporator of FIG. 6.
Figure 8:
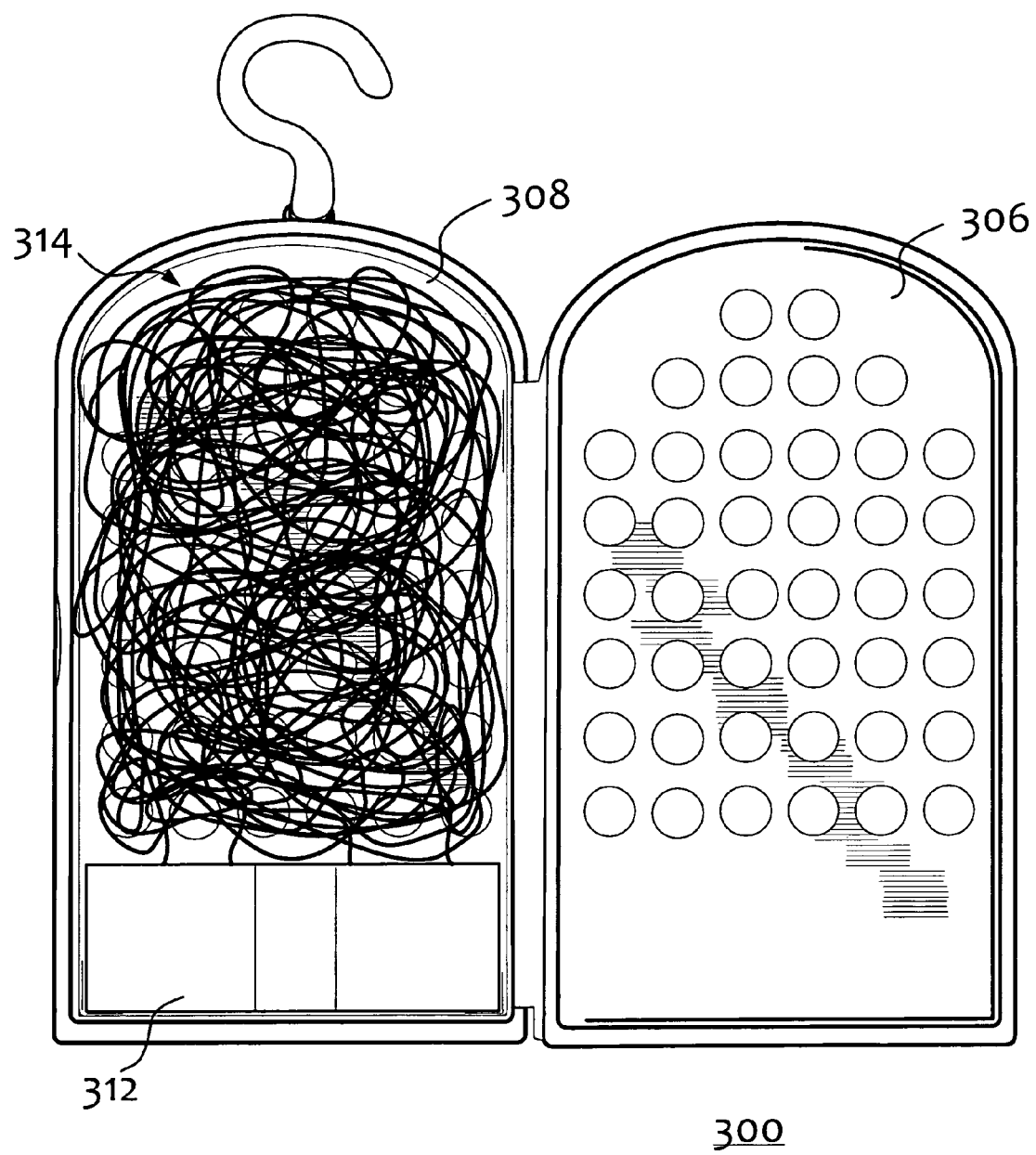
FIG. 8 is a front elevational view of the cedar oil evaporator of FIG. 6 further showing the interior thereof.
Figure 9:
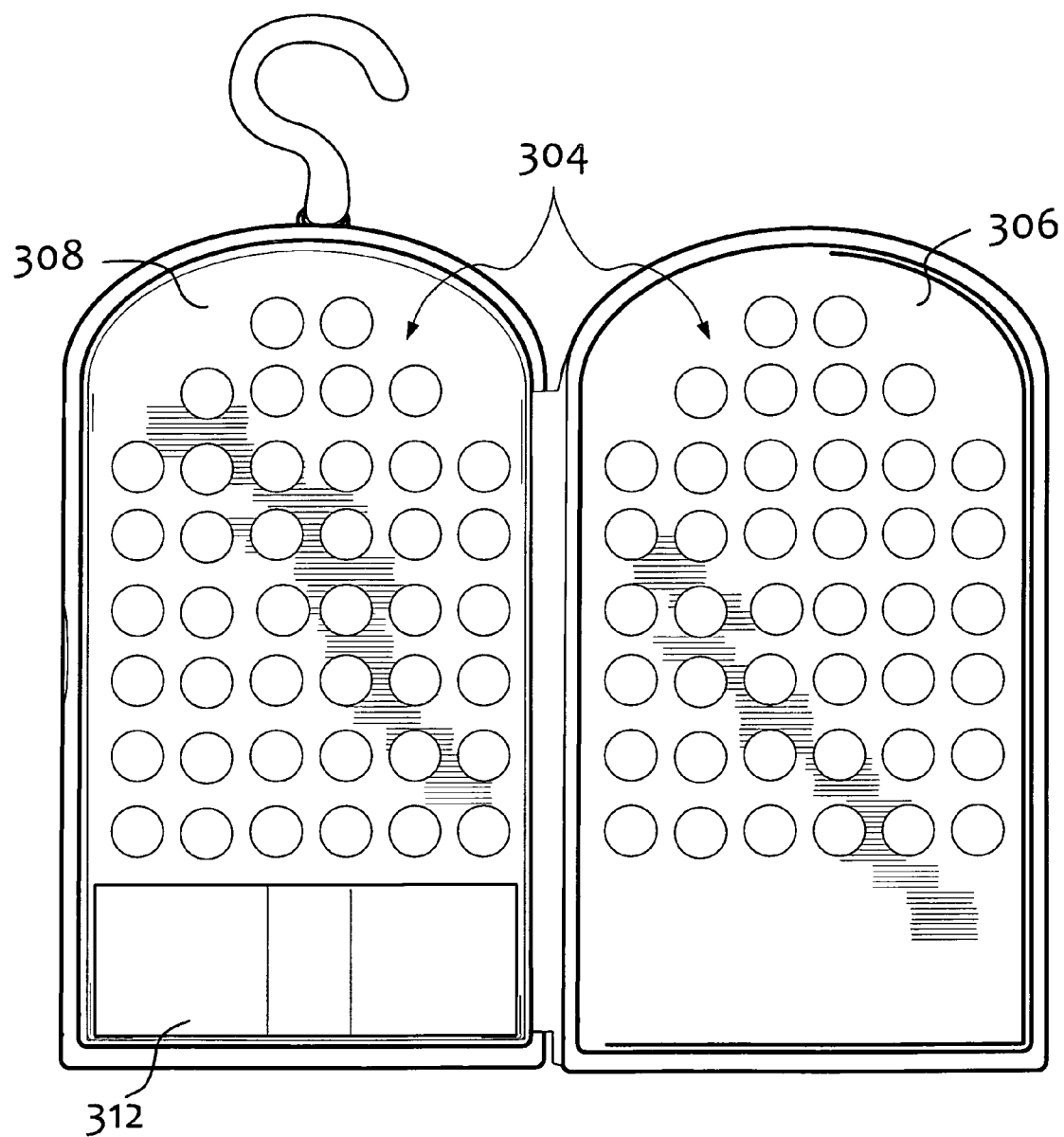
FIG. 9 is a front elevational view similar to that of FIG. 8, wherein the cotton-twine wicks have been omitted for clarity of illustration.

5, wherein a door 306 of a housing 302 of the evaporator 300 is open for showing the interior thereof; FIG. 7 is a perspective view similar to that of FIG. 6, wherein the cotton-twine wicks 310 have been omitted for clarity of illustration; FIG. 7A is a perspective exploded view of certain of the components of the cedar oil evaporator 300; FIG. 8 is a front elevational view of the cedar oil evaporator 300 further showing the interior thereof, and FIG. 9 is a front elevational view similar to that of FIG. 8, wherein the cotton-twine wicks 310 again have been omitted for clarity of illustration. Like the cedar oil evaporator 200, the cedar oil evaporator 300 also is preferably intended for use in a closet.

The cedar oil evaporator 300 includes openings 304 formed in the door 306 and in a back wall 308 of the housing 302, which openings 304 are for the ventilation of air therethrough. The evaporator 300 further includes four separate lengths 310 of cotton twine. Each length 310 of cotton twine extends from a single container or reservoir 312 of cedar oil (or reservoir of cedar oil). Each length 310 serves as a carrier and includes a portion thereof that is immersed in the cedar oil within the reservoir 312 for wicking of the cedar oil out of the reservoir. Furthermore, each length 310 of cotton twine preferably has a great length with the portion of the cotton twine that is immersed in the reservoir 312 being a very small extent of the overall length 310 of the cotton twine. Indeed, this immersed portion preferably represents 10% or less of the overall length 310 of the cotton twine. The remainder of each of cotton twine length 310 is randomly contained within the interior space of the evaporator 300 (i.e., bunched as shown 314 in FIGS. 6 and 8) in such a manner that a large surface area of each of the cotton twine lengths 310 is exposed to air that passes through the ventilation openings 304 in the housing 302. It is believed that the cedar oil is wicked from the reservoir 312 through each extent of the cotton twine lengths 310 and is dispersed via the ventilated air. The evaporator 300 further includes a hook 316 that is attached to and extends from the top of the housing 302 of the evaporator 300 for the preferred hanging of the evaporator 300 in a closet.

As will be appreciated from the foregoing, the cedar oil evaporator 300 is similar to evaporator 200 except principally in the inclusion of a single reservoir 312 of cedar oil rather than four separate reservoirs in the form of the bottles 212.

With further regard to the single reservoir 312, the reservoir 312 includes a base 318 and a cover 320 with four openings 322 formed therein. Each of the four cotton twine lengths 310 extends from a respective one of the opening 322.

In each of the illustrated evaporator 200,300, each of the cotton twine lengths 210,310 (also sometimes referred to as the carrier) preferably is one-sixteenth of an (1/16) inch in diameter and includes an overall length of twelve and one-half (12½) feet. By comparison, the extent of each of the cotton twine lengths 210,310 that is immersed in cedar oil preferably is only a few inches.

Figure 10:
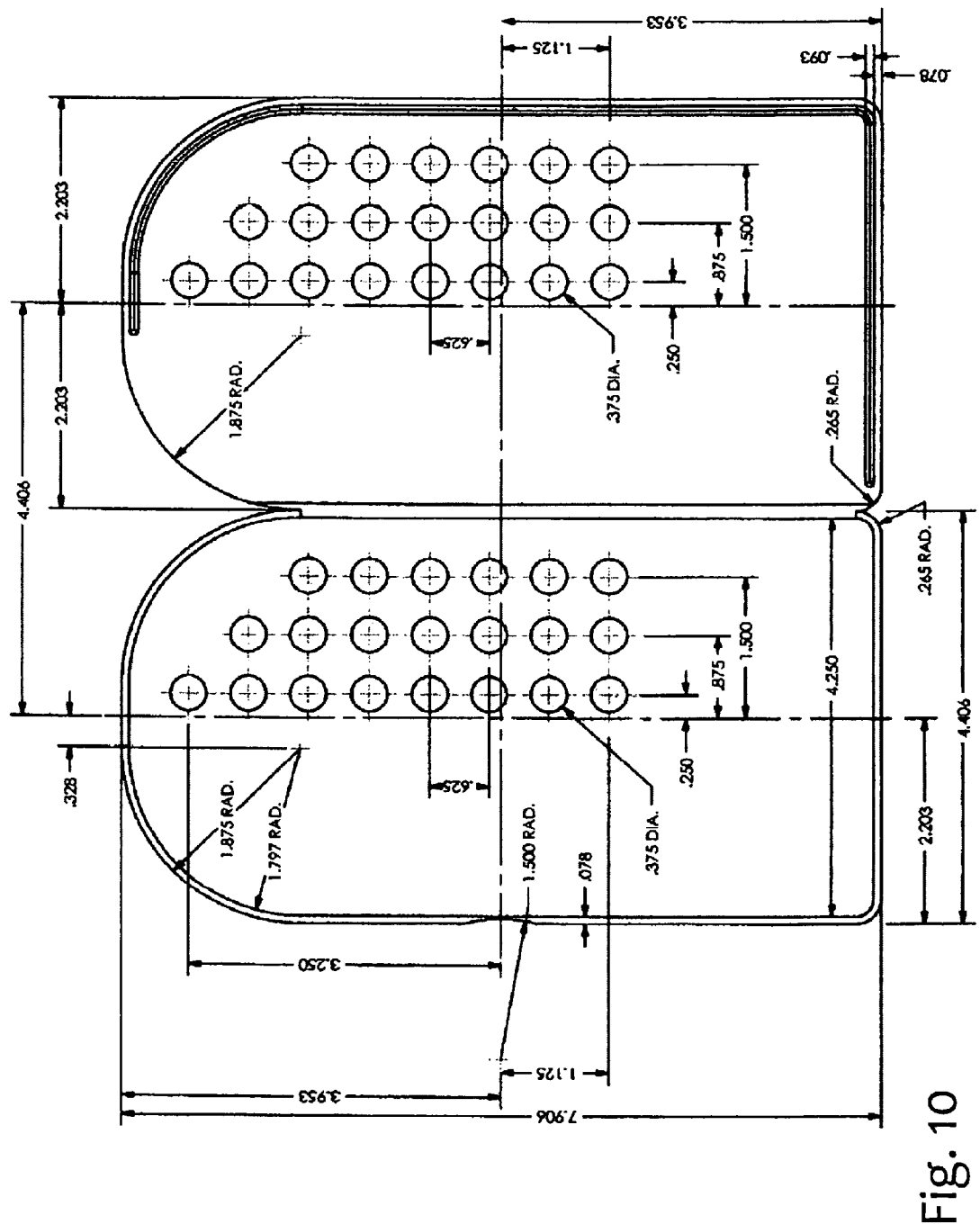
FIG. 10 is an engineering drawing illustrating a front elevational view of a housing component of a cedar oil evaporator in accordance with the third illustrated embodiment of the invention.
Figure 11:
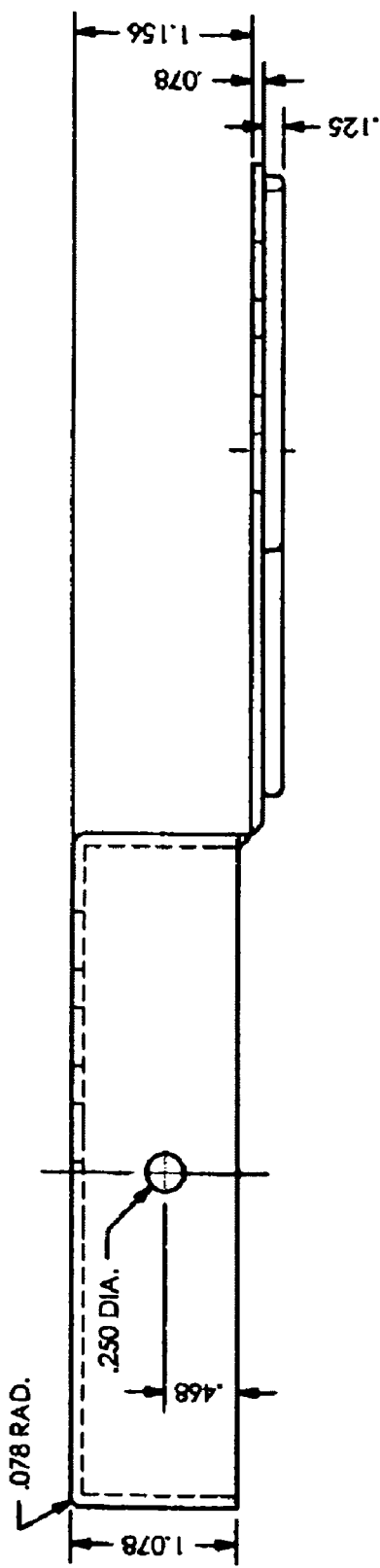
FIG. 11 is an engineering drawing illustrating a top plan view of the housing component of FIG. 10.
Figure 12:
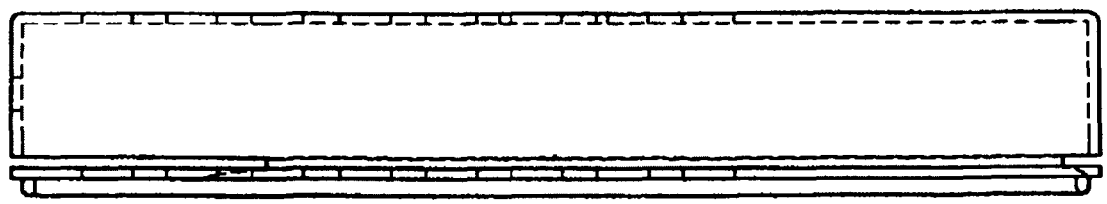
FIG. 12 is an engineering drawing illustrating a side elevation view of the housing component of FIG. 10.
Figure 13:
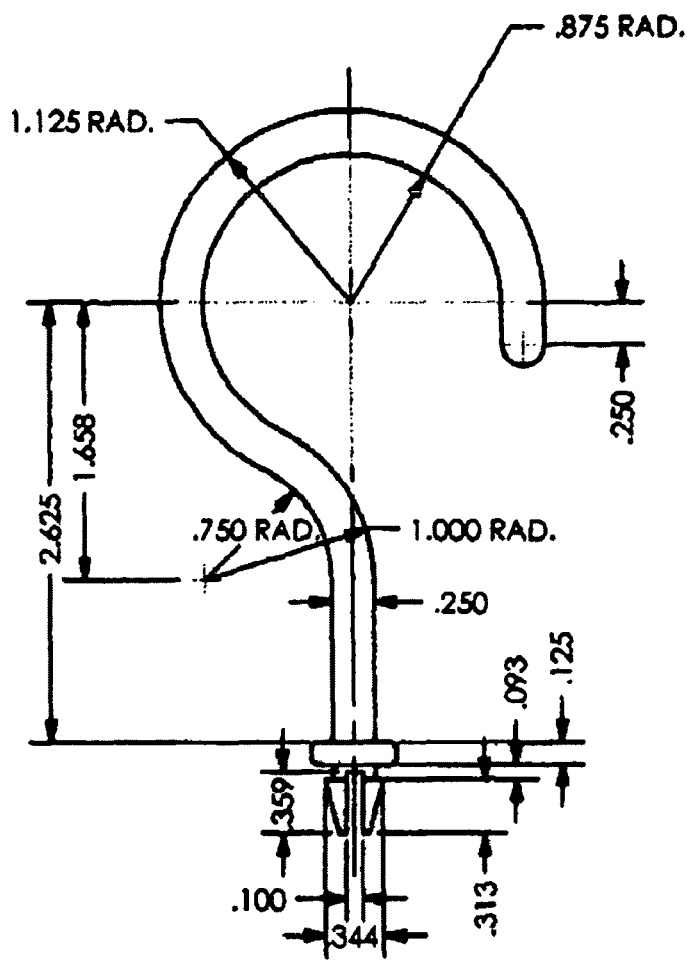
FIG. 13 is an engineering drawing illustrating a front elevational view of a hook of a cedar oil evaporator in accordance with the third illustrated embodiment of the invention.
Figure 14:
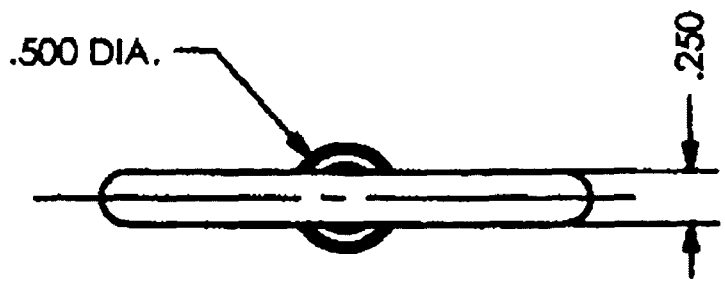
FIG. 14 is an engineering drawing illustrating a top plan view of the hook of FIG. 13.
Figure 15:
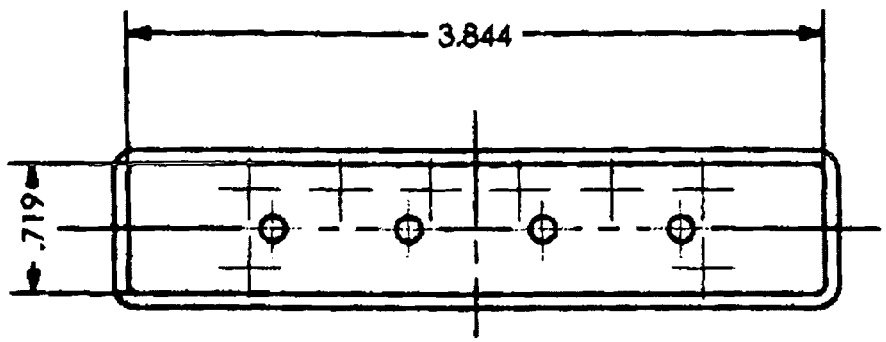
FIG. 15 is an engineering drawing illustrating a bottom plan view of a reservoir cover of a cedar oil evaporator in accordance with the third illustrated embodiment of the invention.
Figure 16:
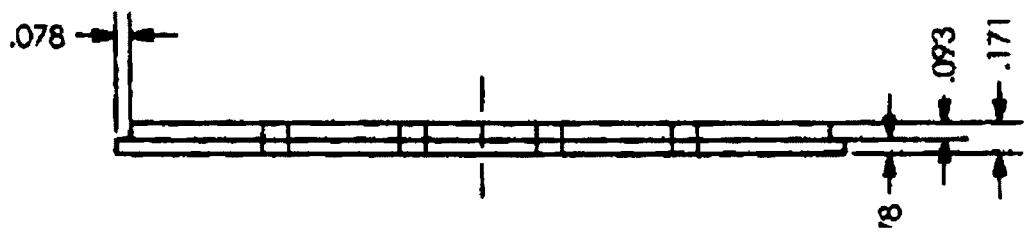
FIG. 16 is an engineering drawing illustrating a cross-sectional view of the reservoir cover of FIG. 15.
Figure 17:
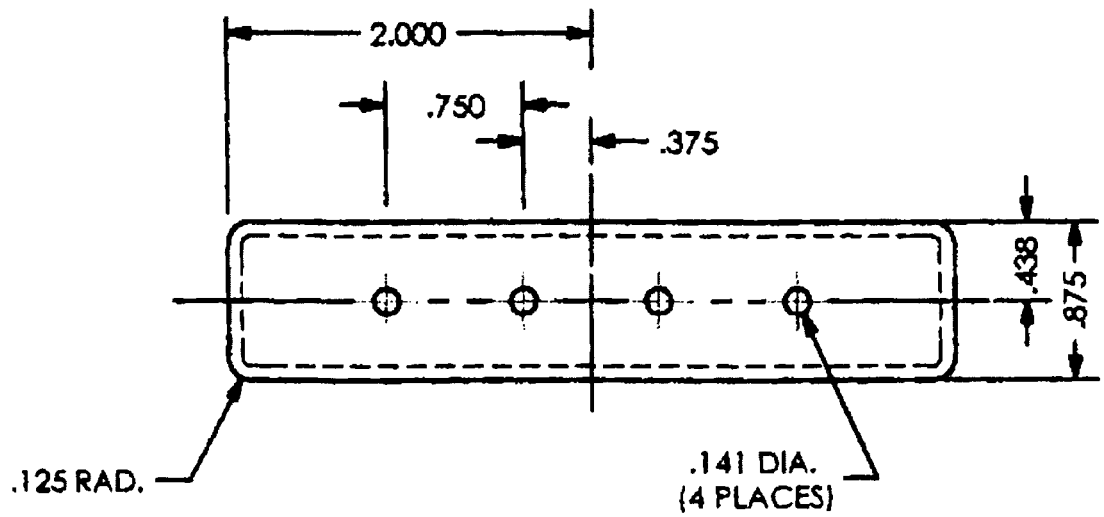
FIG. 17 is an engineering drawing illustrating a top plan view of the reservoir cover of FIG. 15.
Figure 20:
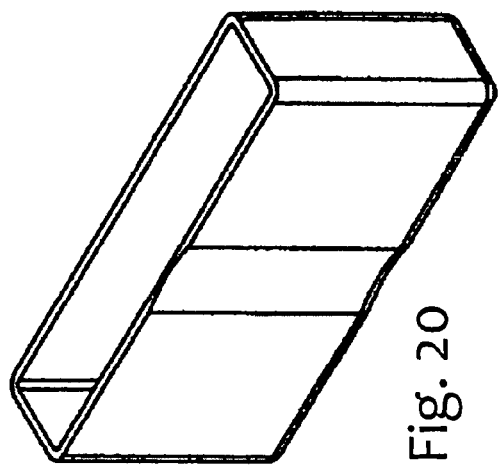
FIG. 20 is an engineering drawing illustrating a perspective view of the reservoir of FIG. 18.
Figure 21:
FIG. 21 is an engineering drawing illustrating a side elevational view of the reservoir of FIG. 18.
Figure 18:
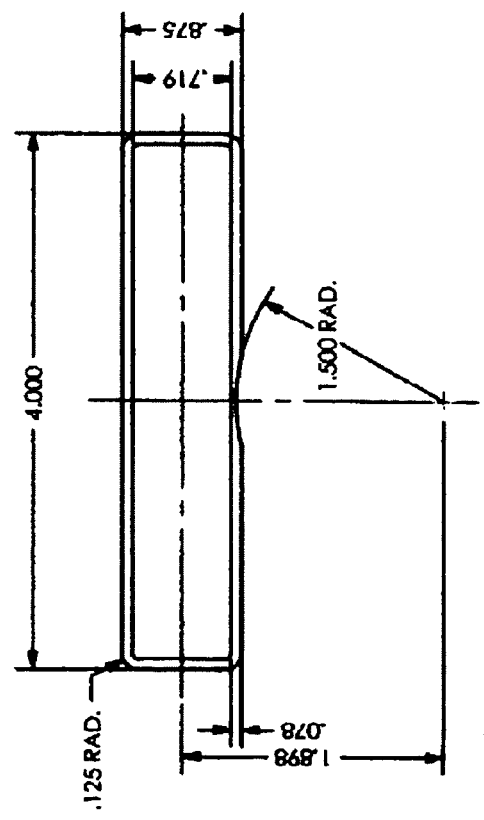
FIG. 18 is an engineering drawing illustrating a top plan view of a reservoir of a cedar oil evaporator in accordance with the third illustrated embodiment of the invention.
Figure 19:
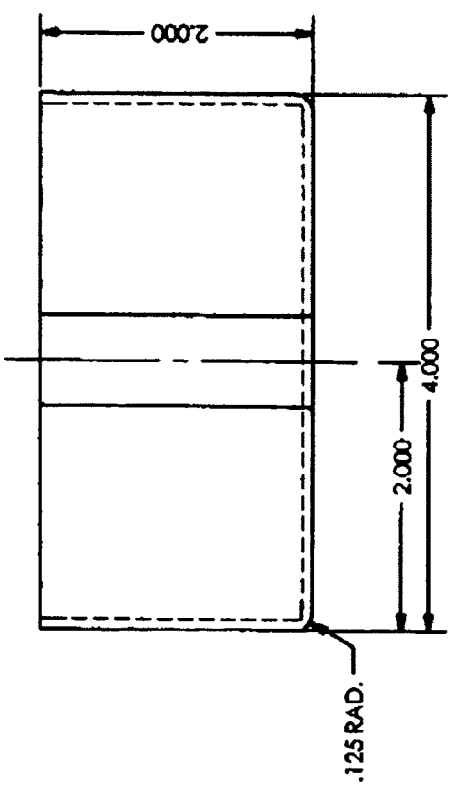
FIG. 19 is an engineering drawing illustrating a front elevational view of the reservoir of FIG. 18.

Engineering drawings of a commercial embodiment of an evaporator in accordance with the invention, and representative of evaporator 300, are illustrated in FIGS. 10-21. These engineering drawing include preferred dimensions as shown therein. It will be appreciated by an ordinary artisan that when used with cotton twine lengths 310 which include an overall length of twelve and one-half (12½) feet as disclosed hereinabove, the overall length of each carrier will be an order of magnitude larger than the greatest dimension of the housing of the evaporator, i.e. seven and nine hundred and six thousandths (7.906) of an inch, which dimension is illustrated in FIG. 10.

In use, the cotton twine lengths 210,310 may be immersed in cedar oil when the evaporators 200,300 are first installed in a closet whereby the cedar oil that initially evaporates therefrom is replaced with cedar oil wicked from a respective reservoir of the evaporators 200,300.

Having now described in detail the illustrated evaporators, it is noted that a feature found in each of the three illustrated embodiments is the use of a carrier or wick that has a very large surface area that is exposed to air for the evaporation of cedar oil. Indeed, with respect to the second and third illustrated embodiments, these devices with their reservoirs are intended to be used in closets for providing a sufficient amount of evaporation of cedar oil so as to provide an equivalent to new or revitalized cedar closets, i.e., it is believed that the second and third illustrated embodiments provide the equivalent protection against moths as a new or revitalized cedar closet.

With regard to the devices disclosed and described in the "Background of the Invention" section above, it is believed that the devices of Travis and Galler provide an insufficient surface area for evaporation of cedar oil so as to enable a sufficient amount of cedar oil to evaporate in order to provide emulation of a cedar closet over the course of several months. Moreover, as cedar oil is believed to be much less volatile than perfumes and deodorizers, the prior art evaporators of U.S. Pat. Nos. 6,921,025; 4,621,768; and 4,352,457 are intended and designed for use with performs and deodorizers, and not with cedar oil, and therefore also are believed to provide an insufficient surface area for evaporation of cedar oil so as to enable a sufficient amount of cedar oil to evaporate in order to provide emulation of a cedar closet over the course of several months.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

For instance, while the carriers in the evaporators 200,300 have each been described as a length of cotton twine 210,310, it is contemplated within the scope of the invention that these lengths of cotton twine may be separate and distinct from each other or, alternatively, may be part of a single length of cotton twine, or any combination thereof.

What is claimed is:

1. A cedar oil evaporator, comprising:
   (a) a housing having openings therein for the ventilation of air;
   (b) a reservoir contained within the housing;
   (c) cedar oil contained within the reservoir; and
   (d) a plurality of carriers partially immersed in the cedar oil configured to wick cedar oil away from the reservoir for dispersing cedar oil via air that passes through the housing,
   (e) wherein each carrier includes first and second extents, (i) the first extent of each respective carrier representing ten percent or less of the overall length of the respective carrier being received within the reservoir, and (ii) the second extent of each respective carrier representing the remainder of the overall length of the respective carrier being randomly coiled within the housing such that a plurality of interstices arc defined, whereby a surface area of the carrier is exposed to air that passes through the ventilation openings in the housing;

(f) wherein the overall length of each carrier is greater than the greatest dimension of the housing;

(g) wherein the interstices include interstices of differing sizes, at least some of the interstices having an area greater than a cross-sectional area of any of the carriers;

(h) wherein at least some of the interstices arc defined collectively by more than one carrier of the plurality of carriers; and (i) wherein each carrier is disposed entirely within the housing;

(j) wherein at least one complete coil is formed by each of the randomly coiled second extents of the plurality of carriers.

2. The cedar oil evaporator of claim 1, wherein there are four carriers.

3. A cedar oil evaporator, comprising:

(a) a housing having openings therein for the ventilation of air;

(b) a reservoir contained within the housing and configured to contain cedar oil;

(c) a plurality of carriers configured to wick cedar oil away from the reservoir for dispersing cedar oil via air that passes through the housing, (d) wherein each carrier includes first and second extents, (i) the first extent of each respective carrier representing ten percent or less of the overall length of the respective carrier being received within the reservoir, and (ii) the second extent of each respective carrier representing the remainder of the overall length of the respective carrier being randomly coiled within the housing such that a plurality of interstices arc defined, whereby a surface area of the carrier is exposed to air that passes through the ventilation openings in the housing;

(e) wherein the overall length of each carrier is an order of magnitude greater than the greatest dimension of the housing;

(f) wherein the interstices include interstices of differing sizes, at least some of the interstices having an area greater than a cross-sectional area of any of the carriers;

(g) wherein at least some of the interstices are defined collectively by more than one carrier of the plurality of carriers (h) wherein each carrier is disposed entirely within the housing; and (i) wherein at least one complete coil is formed by each of the randomly coiled second extents of the plurality of carriers.

4. The cedar oil evaporator of claim 3, wherein there are four carriers.

5. The cedar oil evaporator of claim 3, wherein each carrier comprises a length of cotton twine.

6. The cedar oil evaporator of claim 3, wherein each carrier comprises a length of material having a diameter that is approximately one-sixteenth of an inch or smaller.

7. The cedar oil evaporator of claim 3, wherein each carrier comprises a length of material that is approximately twelve and one-half feet or longer.

8. The cedar oil evaporator of claim 3, wherein each carrier is made from a length of cotton twine that is approximately twelve and one-half feet or longer and that has a diameter that is approximately one-sixteenth of an inch or smaller.

9. The cedar oil evaporator of claim 3, wherein the reservoir comprises a basin and a cover, the basin and cover defining an interior space for holding of the cedar oil, and wherein the cover includes a plurality of openings for receipt therethrough of the plurality of carriers.

10. The cedar oil evaporator of claim 3, wherein the reservoir is removable from the housing.

11. The cedar oil evaporator of claim 3, wherein the housing includes a door that is movable about a hinge between a first position, wherein an interior space of the housing is accessible for removal of the reservoir from the housing, and a second position, wherein the interior space of the container is inaccessible for removable of the reservoir from the housing.

12. The cedar oil evaporator of claim 3, wherein the reservoir includes cedar oil and wherein each of the carriers is partially immersed in the cedar oil within the reservoir.

* * * * *